United States Patent [19]

Hallenburg et al.

[11] Patent Number: 4,808,344

[45] Date of Patent: Feb. 28, 1989

[54] PROCESS FOR RECOVERING AND PURIFYING UNREACTED ACRYLONITRILE FROM THE WASTE STREAM IN THE MANUFACTURE OF 2-ACRYLAMIDO-2-METHYL PROPANE SULFONIC ACID

[75] Inventors: Douglas J. Hallenburg; Alan C. Clark, both of Mentor; James L. Hambrick, Chesterland, all of Ohio

[73] Assignee: The Lubrizol Corporation, Wickliffe, Ohio

[21] Appl. No.: 154,666

[22] Filed: Feb. 10, 1988

Related U.S. Application Data

[63] Continuation of Ser. No. 896,545, Aug. 13, 1986, abandoned.

[51] Int. Cl.$^4$ .................. B01D 3/10; C07C 121/32; C07C 143/02
[52] U.S. Cl. .................. 260/513 N; 203/29; 203/36; 203/37; 203/47; 203/72; 203/78; 203/80; 203/94; 203/DIG. 3; 558/463
[58] Field of Search .................. 203/DIG. 3, 29, 33, 203/36, 37, 38, 47, 72, 78, 80, 91, 94, 98, 89, 100; 558/466, 463, 465; 260/513 N; 202/177; 159/49, 13.1

[56] References Cited

U.S. PATENT DOCUMENTS

| | | | |
|---|---|---|---|
| 2,361,367 | 10/1944 | Davis et al. | 260/513 N |
| 2,653,966 | 9/1953 | Taylor et al. | 558/465 |
| 2,987,451 | 6/1961 | Sennewald et al. | 203/DIG. 3 |
| 3,051,630 | 8/1962 | Hadley et al. | 202/71 |
| 3,329,582 | 7/1967 | Sennewald et al. | 203/72 |
| 3,459,639 | 8/1969 | Borrel et al. | 203/37 |
| 4,061,858 | 12/1977 | Wild et al. | 558/463 |
| 4,108,734 | 8/1978 | Kwasnoski et al. | 203/47 |
| 4,219,498 | 8/1980 | Doi et al. | 260/513 |
| 4,377,444 | 3/1983 | Wu | 203/96 |
| 4,384,924 | 5/1983 | Thoma | 203/47 |
| 4,404,064 | 9/1983 | Lovett | 203/84 |

FOREIGN PATENT DOCUMENTS 52-62226  5/1977  Japan ......... 558/463

Primary Examiner—Wilbur Bascomb
Attorney, Agent, or Firm—Karl Bozicevic; Robert A. Franks; William C. Tritt

[57] ABSTRACT

Excess amounts of a pure form of acrylonitrile are reacted with other reactants in the production of various compounds such as 2-acrylamido-2-methyl propane sulfonic acid. Accordingly, large amounts of acrylonitrile remain unreacted and present with other contaminants. The present invention is directed toward the purification of such unreacted acrylonitrile and the purified acrylonitrile obtained from such a purification process. The purification is carried out by treating the unreacted acrylonitrile with a base and removing salts formed. The treated material is fed to a heat exchanger which heats the material preferably under vacuum to about 120° F. and provides a heated fluid material. This heated fluid material is pumped to a lower area of a distillation tower which is maintained under vacuum and includes a plurality of distillation trays. Purified acrylonitrile has a lower boiling point and is drawn toward the top of the tower by vacuum and removed whereas the remainder of the material which includes contaminants has a higher boiling point and falls to the bottom of the tower. This bottom portion is removed and recycled to the heat exchanger. The purified acrylonitrile removed from the top of the tower by vacuum is capable of, and sufficiently pure for, reuse in the formation of other compounds such as 2-acrylamido-2-methyl propane sulfonic acid. The process provides purified acrylonitrile while avoiding undesirable polymerization. The purified acrylonitrile obtained from the proces and 2-acrylamido-2-methyl propane sulfonic acid produced with the purified acrylonitrile lack undesirable water insoluble polymers and copolymers and have improved and unexpectedly superior storage stability.

14 Claims, 1 Drawing Sheet

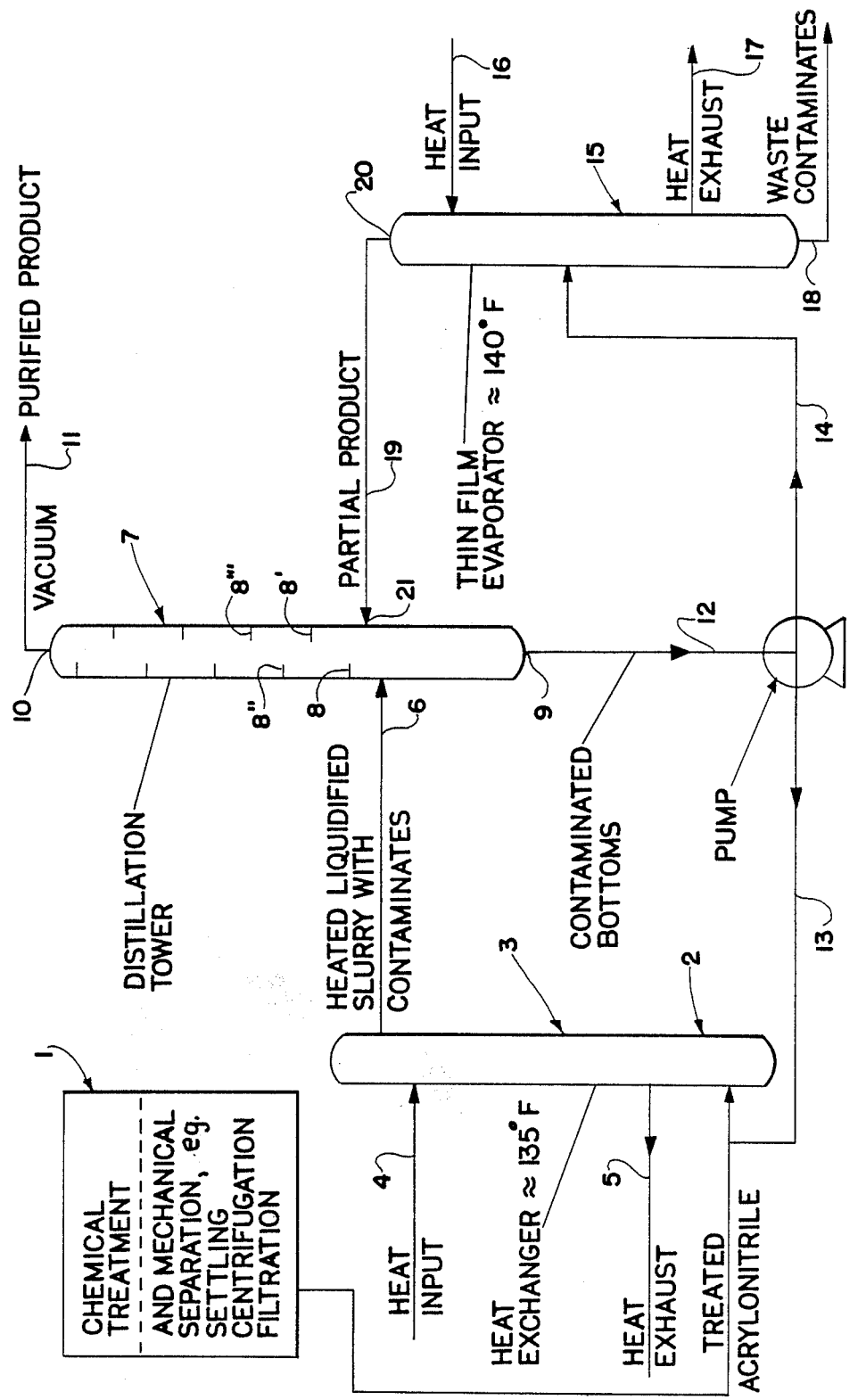

PROCESS FOR RECOVERING AND PURIFYING UNREACTED ACRYLONITRILE FROM THE WASTE STREAM IN THE MANUFACTURE OF 2-ACRYLAMIDO-2-METHYL PROPANE SULFONIC ACID

This is a continuation of copending application Ser. No. 896,545 filed on Aug. 13, 1986 and now abandoned.

BACKGROUND OF THE INVENTION

There are many procedures for the production of acrylonitrile. This compound has become one of the most important and promising organic chemical intermediates available. It is a particularly desirable intermediate in the manufacture of a wide range of products, for example, plastics, synthetic rubber, synthetic fibers, soil conditioners and the like. For many uses, acrylonitrile must be of high purity and, for this reason, strict specifications must be met in the commercial manufacture of acrylonitrile.

"Each of the commercial procedures used for the preparation of acrylonitrile produces its own set of impurities and by-products and each presents its own problems of purification." (See U.S. Pat. No. 3,459,639.)

Different purification processes are required in that different processes for making acrylonitrile result in the formation of different by-product contaminants. Accordingly, different procedures may be required to remove the contaminants and purify the acrylonitrile. Due to such constraints, any given acrylonitrile purification process is not likely to be universally interchangeable with respect to its usefulness in the purification of all acrylonitrile containing compositions.

As indicated in U.S. Pat. No. 4,404,064, one very good and commercially practiced method of producing olefinically unsaturated nitriles is the catalytic reaction of ammonia and an olefin. For example, acrylonitrile and methacrylonitrile may be produced by the vapor phase catalytic oxidation of propylene and isobutylene, respectively, in the presence of ammonia. In these processes, significant amounts of impurities are produced. The production of acrylonitrile from ammonia and propylene results in the formation of significant quantities of acetonitrile, propionitrile, acetone and the like. It is necessary to remove these by-product impurities to produce an unsaturated nitrile suitable for polymerization to other products.

U.S. Pat. No. 3,459,639 to Borrel et al discloses a process for the purification of a complex mixture of acrylonitrile, acetonitrile and other materials formed in the vapor phase conversion of acrolein or propylene to acrylonitrile over a catalyst in the presence of ammonia and oxygen. Separation of acrylonitrile from acetonitrile is accomplished by extractive distillation using deionized water at a pH of at least 5 and preferably 5–7 with the introduction of an alkaline agent to the distillation mixture.

U.S. Pat. No. 4,377,444 to Wu relates to the recovery and purification of olefinic nitriles and more particularly pertains to an improved process for the recovery and purification of olefinic nitriles, such as methacrylonitrile and acrylonitrile, produced by the ammoxidation of isobutylene and propylene from mixtures of said olefinic nitriles with such materials as acetonitrile, hydrogen cyanide, propionitrile, butyronitrile, methacrolein, acrolein, acetone, acetaldehyde, etc.

Wu points out that when an olefin, such as isobutylene or propylene, is allowed to react with ammonia and molecular oxygen in the vapor phase at elevated temperatures and in the presence of an ammoxidation catalyst, the corresponding olefinic nitriles, such as methacrylonitrile and acrylonitrile, are produced along with varying amounts of by-products of the ammoxidation reaction including acetonitrile, hydrogen cyanide, propionitrile, butyronitrile, methacrolein, acrolein, acetone, acetaldehyde, and mixtures of the desired olefinic nitrile, and some of these by-products appear in the ammoxidation reactor effluent.

In accordance with the Wu process, the products of the ammoxidation reaction are recovered in a first step by absorption in water during which step some heavy or high-boiling organic compounds are formed through polymerization, condensation, etc., of some of the lighter organic products. Accordingly, the Wu process is an improved method for separating the olefinic nitriles from the by-products formed in the ammoxidation reaction as well as from the heavy organic compounds.

The process disclosed in U.S. Pat. No. 3,051,630 to Hadley et al also relates to the purification of acrylonitrile. However, this process is particularly applicable to the purification of acrylonitrile produced by the catalytic vapor phase reaction of acrolein with ammonia and molecular oxygen. In such reactions, the crude acrylonitrile is usually recovered in the form of a dilute aqueous solution, which also contains varying amounts of acrolein and hydrogen cyanide, by contacting the gaseous reaction product with water, preferably after neutralization of any unreacted ammonia.

Once a purified form of acrylonitrile is obtained, the acrylonitrile monomer is used to produce a variety of products as indicated above. The present invention relates to a process for purifying acrylonitrile from contaminants when excess amounts of acrylonitrile are reacted with another reactant to produce a product. More specifically, the product produced using excess amounts of acrylonitrile (which is itself an intermediate) is 2-acrylamido-2-methyl propane sulfonic acid (sold under the trademark AMPS$^R$ by The Lubrizol Corporation). During the production of AMPS$^R$ stoichiometric excesses of acrylonitrile are used. Accordingly, varying amounts of acrylonitrile remain unreacted and are present with other contaminants after the desired product is formed and separated away. These contaminants are often quite reactive with acrylonitrile causing polymerization, more specifically causing undesired copolymerization of acrylonitrile monomer units with monomer units of contaminants present. If the unreacted acrylonitrile which is present with contaminants is merely recycled in the synthesis of the 2-acrylamido-2-methyl propane sulfonic acid, the resulting product does not have the desired degree of purity and will not meet desired specifications. Further, any such contaminated acrylonitrile could initiate unwanted polymerization. In addition, any reaction product (such as 2-acrylamido-2-methyl propane sulfonic acid) produced from such contaminated acrylonitrile would not have the desired specifications, e.g., lack of water insoluble polymerized particles, degree of purity, etc. Accordingly, the present inventors have developed an improved process for the purification of such unreacted acrylonitrile.

As pointed out above, processes for purifying acrylonitrile vary based on factors such as the contaminants present with the acrylonitrile. The present invention is different from the processes discussed above in that those processes relate generally to the purification of waste from acrylonitrile production whereas the present process relates to the purification of unreacted acrylonitrile from the waste stream created during the manufacture of a product (such as 2-acrylamido-2-methyl propane sulfonic acid) produced using excess amounts of acrylonitrile. In other words, the present invention is directed to a process for purifying unreacted acrylonitrile when the acrylonitrile had been used as a reactant to produce another product and the prior art such as that discussed above is generally directed to purifying acrylonitrile away from unreacted reactants used to produce acrylonitrile. These unreacted reactants formed while producing acrylonitrile are generally less reactive than the contaminants present with the unreacted acrylonitrile from making 2-acrylamido-2-methyl propane sulfonic acid. The more reactive the contaminants the greater the need for removing such contaminants.

When different reactants are used, different contaminants result. Accordingly, no one process is necessarily interchangeably useful in connection with purifying acrylonitrile away from all types of contaminants.

SUMMARY OF THE INVENTION

In order to synthesize 2-acrylamido-2-methyl propane sulfonic acid, excess amounts of acrylonitrile are combined with sulfuric acid and isobutene. The resulting reaction product includes 2-acrylamido-2-methyl propane sulfonic acid along with substantial amounts of unreacted acrylonitrile and other by-products. The 2-acrylamido-2-methyl propane sulfonic acid can be separated away leaving the acrylonitrile present along with various residual acids, acrylamides, and other by-product contaminants. The contaminants are present in an amount of about 1–2 percent by weight based on the weight of the composition.

The acid contaminants include sulfuric acid, isobutylene monosulfonic acid, isobutylene disulfonic acid and small amounts of 2-acrylamido-2-methyl propane sulfonic acid, t-butyl acrylamide and acrylamide. If the acrylonitrile containing the 1 to 2 percent contaminants such as the residual acids is reused for the production of the 2-acrylamido-2-methyl propane sulfonic acid, the resulting product (i.e., the 2-acrylamido-2-methyl propane sulfonic acid) will have various undesirable characteristics. For example, the resulting product will contain undesirable polymerized material formed by the polymerization of acrylonitrile monomers with contaminant monomers. Accordingly, it is desirable to purify the acrylonitrile before it is reused, and the present invention is directed to such a purification process and the product resulting therefrom.

The unreacted acrylonitrile containing contaminants such as the residual acids is first neutralized by adding a base such as NaOH, NH$_3$, Ca(OH)$_2$ or lime (i.e., calcium oxide) and/or mixtures thereof which react with contaminant acids present forming various salts, e.g., calcium slats. Ammonia may be used under anhydrous conditions, but lime is the preferred base and is used in the presence of a catalytic amount of water. The present inventors have found that the lime and water together work particularly well for neutralization in connection with the present invention. The amount of lime added is dependent upon the acid neutralization number of the contaminated acrylonitrile to be treated. The neutral salts which are formed as solids precipitate out or can be separated away along with any unreacted lime via settling or by the use of any mechanically enhanced means, e.g., centrifuge, or filtration.

At this point, although the acrylonitrile product has been neutralized and purified to a certain extend, it still includes contaminants which would interfere with the use of the acrylonitrile in the synthesis of other materials such as 2-acrylamido-2-methyl propane sulfonic acid. Accordingly, after the removal of the neutral salts, the contaminated acrylonitrile is fed to a heat exchanger which operates at a relatively low temperature (i.e., below 172° F. and preferably in the range of 110° F. to 140° F.) under vacuum so that all the material present is heated to a temperature in the desired range.

The heated material in the heat exchanger which includes liquid and vapor is then transferred to a lower portion of a distillation tower. The tower is comprised of a lower opening, a plurality of distillation trays and an upper opening, with the tower being maintained under vacuum. A majority of the heated material entering the distillation tower falls to the bottom of the tower whereas a small amount of purified acrylonitrile rises to the top of the tower and is evacuated therefrom via a pressure differential.

The heated material falling to the bottom of the distillation tower is, (in accordance with a first embodiment) returned to the heat exchanger and in accordance with a second embodiment, divided into two portions with the major portion being returned to the heat exchanger. In accordance with the second embodiment, a minor portion of the material falling to the bottom of the distillation tower is transferred to a thin film evaporator which is maintained under vacuum at a temperature above the melting point and below about 172° F. and preferably in the range of about 120° F. to about 145° F. Within the thin film evaporator, contaminated wastes containing relatively high amounts of residual acids fall to the bottom of the evaporator and a partially purified acrylonitrile product is removed from the top of the evaporator and transferred to the distillation tower. This partially purified material is transferred to the distillation tower at a point preferably above where material enters the tower from the heat exchanger but below the trays in the tower.

The partially purified acrylonitrile product transferred to the distillation tower from the thin film evaporator of the second embodiment is then subjected to further distillation within the vacuum maintained within the distillation tower. A highly purified acrylonitrile product is removed from the top opening of the distillation tower in accordance with both the first and second embodiments. Contaminants within the distillation tower continue to fall to the bottom of the tower and are removed. Most of the contaminated material is recycled to the heat exchanger per the first embodiment and, per the second embodiment, is divided into two portions with the major portion being recycled to the heat exchanger and a minor portion being directed to the thin film evaporator. Accordingly, the process is continually carried out as purified acrylonitrile product is removed from the top of the distillation tower.

The purified acrylonitrile product removed from the upper portions of the distillation tower contains negligible amounts of contaminants such as residual acids and acrylamides. Accordingly, this purified acrylonitrile itself has the desired average molecular weight and excellent storage stability. Further, the purified acrylonitrile can be utilized in the production of other materials such as being recycled for use in the production of 2-acrylamido-2-methyl propane sulfonic acid which will also have a high degree of purity. This high degree of purity is particularly important to obtain when eliminating contaminants which are particularly reactive with the acrylonitrile. Such reactive contaminants react with the acrylonitrile to form water insoluble polymers which cloud up aqueous solutions prepared by including 2-acrylamido-2-methyl propane sulfonic acid with water.

A primary object of the present invention is to provide a method for purifying contaminated acrylonitrile waste stream resulting from the synthesis of a compound produced by reacting a reactant with an excess of acrylonitrile to obtain a product.

A feature of the present invention involves neutralizing residual acids present with such unreacted acrylonitrile by treating with a base such as lime or ammonia and removing salts formed.

Another object of the present invention is to provide a method for purifying acrylonitrile which uses vacuum and lower temperatures while being economical and efficient.

An important feature of this invention is that it allows for the purification of such waste stream type contaminated acrylonitrile while avoiding polymerization of the acrylonitrile during purification.

An advantage of the present invention is that it provides a method for purifying acrylonitrile which is environmentally acceptable and in compliance with environmental laws.

Another advantage of the present invention is that it provides an acrylonitrile purification process which reduces the build up of deposits on equipment in that polymerization is reduced greatly, and salts formed are removed early in processing.

An important feature of the present invention is that it provides a means whereby unreacted acrylonitrile used in the production of 2-acrylamido-2-methyl propane sulfonic acid can be reused to produce a purified product such as 2-acrylamido-2-methyl propane sulfonic acid having the desired characteristics such as storage stability and the lack of high molecular weight water insoluble polymers formed by the reaction of acrylonitrile with various reactive contaminants.

Yet another object of the present invention is to provide a means for producing purified acrylonitrile which itself has the desired specifications such as the lack of high molecular weight water insoluble polymers and improved and unexpectedly superior storage stability.

Another feature of the present invention is that it provides purified acrylonitrile which has the desired specifications and can form 2-acrylamido-2-methyl propane sulfonic acid which can provide a clear aqueous solution.

These and other objects, advantages and features of the present invention will become apparent to those skilled in the art upon reading the present disclosure.

BRIEF DESCRIPTION OF THE DRAWING

FIG. 1 is a schematic plan view of the purification system used in a preferred embodiment of the present invention.

DETAILED DESCRIPTION OF THE INVENTION

The chemical product 2-acrylamido-2-methyl propane sulfonic acid (produced as the product AMPS$^R$, a trademark of The Lubrizol Corporation) is used throughout industry for a variety of different purposes. The 2-acrylamido-2-methyl propane sulfonic acid product, as well as other products, can be produced by reacting an excess amount of acrylonitrile with sulfuric acid and isobutylene. Due to economic and environmental factors, it is desirable to reuse the unreacted acrylonitrile in order to produce more 2-acrylamido-2-methyl propane sulfonic acid. However, the unreacted acrylonitrile is present with other contaminants, such as acrylamides and residual acids; and, as such, has poor storage stability and cannot be reused in the production of 2-acrylamido-2-methyl propane sulfonic acid of high quality. If the acrylonitrile is not purified to the necessary degree, it will react with contaminants present and form water insoluble compounds. In order to produce a high quality 2-acrylamido-2-methyl propane sulfonic acid product and make efficient use of acrylonitrile, the present inventors have discovered a means for the purification of the unreacted contaminated acrylonitrile waste stream generated from the production of 2-acrylamido-2-methyl propane sulfonic acid.

When an excess amount of acrylonitrile is used in the production of 2-acrylamido-2-methyl propane sulfonic acid, the desired 2-acrylamido-2-methyl propane sulfonic acid product formed can be removed leaving behind acrylonitrile present with 1–2 percent by weight of contaminants (such as sulfuric acid, isobutylene monosulfonic acid, isobutylene disulfonic acid, acrylamides and small amounts of 2-acrylamido-2-methyl propane sulfonic acid) which were not successfully removed. This acrylonitrile is the contaminated waste stream acrylonitrile referred to above.

The present inventors have found that in order to effectively purify the unreacted acrylonitrile, it is first desirable to chemically treat the acrylonitrile by neutralizing it with a strong base such as lime (i.e., calcium oxide), NaOH, NH$_3$, or Ca(OH)$_2$. When neutralizing with lime, i.e., calcium oxide, the amount of lime added is dependent upon the acid neutralization number of the acrylonitrile to be treated. Although some results may be obtainable using 0.5 to 1.5 equivalents of lime per acid equivalent of contaminated acrylonitrile, it is not generally desirable to use less than 1.0 equivalent of lime per acid equivalent of acrylonitrile. Further, the present inventors have found that the use of about 1.1 equivalents of lime per acid equivalent of contaminated acrylonitrile is particularly preferred in that the use of less than 1.0 equivalent does not completely neutralize all acid present and the use of more than 1.1 equivalents is not economical.

When using lime to neutralize, water must be present. The solubility of water in acrylonitrile is only about 3.2%. Thus, less than 3.2% water can be used. The present inventors have found that the use of more than about 2.7% water causes the calcium salts to become sticky and hard to handle. It has also been found that at least about 0.5% water must be present in order to provide for an efficient neutralization step. Accordingly, water is preferably present in an amount of about 1.0 to 2.5%, more preferably about 1.5% to about 2.0%.

Anhydrous ammonia may be used, but lime is not effective unless it is used in combination with a catalytic amount of water as described above. The unreacted acrylonitrile which has been treated with the base is neutralized and salts are formed. For example, calcium salts are formed by treating with lime in the presence of a catalytic amount of water. Some of the salts formed will quickly precipitate and can be easily removed along with any unreacted lime. Any salts which do not quickly precipitate can be removed by settling or by subjecting the base-treated material to a mechanically enhanced separation means such as a centrifuge, and/or filtration as schematically shown in block one in the figure.

After carrying out one or more of the mechanical separation means described above, most of the salts formed and unreacted lime have been removed and the acrylonitrile has been purified to a certain extent. However, at this point, the acrylonitrile still contains about 1.5 percent or less of residual contaminants which must be removed by other physical means, i.e., various distillations.

Referring now to the drawings, the base-treated acrylonitrile which has had the salts removed therefrom by precipitation and/or various mechanical means is fed via line 1 to a heat exchanger 2. The rate of feed can vary depending on the particular device and embodiment used. The present inventors have found that a feed rate of about 40 to 100 gal/min to be useful, preferably about 70 gal/min. The heat exchanger 2 is preferably a single pass shell and tube heat exchanger. The present inventors have found it particularly useful to employ a 316 stainless steel single pass shell and tube heat exchanger of about 750 ft$^2$ in size. The contaminated acrylonitrile in the heat exchanger 2 is maintained at a temperature below 172° F. and preferably in the range of about 110° F. to about 140° F., more preferably about 120° F. at about 320 mmHg, by continually circulating a heated fluid (preferably in the form of a saturated steam which is maintained under reduced pressure at a temperature of about in the range of about 185° to about 215° F.) through the outer shell 3 of the heat exchanger 2.

At atmospheric pressure, the temperature of the acrylonitrile must be kept below 172° F. to prevent polymerization. The present inventors have found it desirable to keep the temperature in the range of 110° F/ to about 140° F. while maintaining a vacuum of about 320 mmHg.

The steam temperature and pressure will rise as the internal components of the heat exchanger fouls. However, due to the temperature level, the acrylonitrile is not subjected to a substantial amount of polymerization and any fouling on the components in contact with the acrylonitrile is greatly reduced. This reduction in polymerization and deposit build up on internal surfaces contacting the acrylonitrile is a substantial advantage of the present invention. The heated fluid is forced to flow about the shell 3 by input lines 4 where it is circulated about the shell 3 and then allowed to exit via exhaust lines 5 thus maintaining the acrylonitrile therein at a relatively constant temperature. A number of different factors are interrelated and determinative of whether the acrylonitrile will react with a contaminant. As temperature, pressure, the amount of contaminant and the degree of reactivity of the contaminants increases, the likelihood of forming undesirable polymers and copolymers between contaminants themselves and/or any acrylonitrile is increased.

The acrylonitrile becomes a heated fluid material containing both liquid and vaporous material along with contaminants. The vaporous portion of the material has been freed of some of the contaminants. From the heat exchanger 2, the liquid/vaporous material is pumped via a line 6 (at a temperature below 172° F. and preferably in the range of about 106° F. to about 126° F., more preferably about 116° F.) to a lower area of a distillation tower 7. The tower 7 is comprised of a cylindrical wall portion, the inner side of which has a plurality of distillation trays 8, 8', 8'', 8''', etc., extending therefrom, a bottom opening 9 and an upper opening 10. The tower 7 may vary in size, shape, and number of trays but the present inventors have found that a 316 stainless steel tower with six trays and 19 ft. 8 inches high and 6 ft. in diameter works particularly well with the trays positioned at about two foot internals. The tower 7 may be maintained under vacuum, but is maintained so as to provide a pressure differential between the inside of the tower and the exit line 11, i.e., the pressure inside the tower 7 is greater than in the exit line 11 so that pure vaporized gas (acrylonitrile) flows freely from the tower 7 through exit 10 to line 11. The present inventors have found that the process works particularly well by maintaining the internal temperature of the tower 7 in the range of about 110° F. to about 140° F., more preferably 120° F. at about 320 mmHg. This temperature and pressure range is preferred for a number of reasons, but it should be noted that the temperature might be as high as just below 172° F. and as low as the melting point of acrylonitrile and atmospheric pressure.

Nearly all of the liquified portion of the liquid/vaporous material added to the tower 7 via line 6 falls to the bottom of the tower 7 and exits via the opening 9. Pure acrylonitrile has a lower boiling point and will rise to the top of the tower and be removed from the opening 10 through the line 11. The higher boiling point acrylonitrile present with contaminants will fall to the bottom of the tower 7 and be removed from the opening 9 via the line 12. In accordance with a first embodiment of this invention, nearly all the material removed via the line 12 is pumped to line 13 and into the heat exchanger 3 and is thus recycled. A small amount of highly contaminated bottoms is removed from the bottom of the tower 7.

In accordance with a second embodiment of the present invention, the material being removed via the line 12 is split, and a majority of the material is recirculated to the heat exchanger 2 via line 13 (line 13 may connect directly to the heat exchanger 2 or may feed back into the feed line 1), and a smaller portion of the material from the line 12 is directed via a line 14 to a thin film evaporator 15. The second embodiment also involves removing some contaminated bottoms from the bottom of the tower 7 as well as from the bottom of the thin film evaporator 15 via line 18. The process of the present invention is economically advantageous in that it allows for the economic recovery of large amounts of acrylonitrile without vaporizing a large portion of liquid feed entering the heat exchanger 3. This process also greatly reduces the build up of polymerized material on the equipment by keeping the temperature low and reducing the portion of feed which need be vaporized.

The evaporator 15 is maintained at a temperature below 172° F. and preferably in the range of about 120° F. to about 145° F., more preferably about 120° F. at about 320 mmHg. The temperature may, at atmospheric pressure, be as low as the melting point of the relevant material (i.e., contaminated acrylonitrile) and as high as about 172° F. The inventors have found that a 53.8 ft$^2$ 316 stainless steel evaporator works particularly well. The evaporator is maintained at this temperature by continually circulating a fluid about its outer skin with the fluid entering via input line 16 and exiting via exhaust line 17. The heated fluid entering and exiting via lines 16 and 17 preferably does not enter the evaporator but only serves to regulate the temperature within the evaporator. The inside of the evaporator is maintained under reduced pressure. The higher boiling point material containing large amounts of contaminants falls to the bottom of the evaporator and is removed via the line 18 for further processing and/or disposal. A partially purified and lower boiling point acrylonitrile is removed via a line 19 connected at an upper opening 20 of the evaporator 15. The partially purified acrylonitrile transferred via the line 19 is then directed back to the distillation tower 7 and enters the tower 7 at a point 21 which is preferably above but may be below or even with the lower area of the tower where the liquid/vaporous material enters the tower from the line 6. Much of the partially purified acrylonitrile product entering from the line 19 has a relatively low boiling point and is accordingly drawn to the top of the distillation tower and evacuated via the line 11. The purified material drawn off from the top of the distillation tower 7 through the opening 10 and the line 11 is highly purified. This purified material has improved and unexpectedly superior properties such as molecular weight and storage stability and can be utilized in the production of 2-acrylamido-2-methyl propane sulfonic acid which will also have a desired average molecular weight and improved, unexpectedly superior storage stability.

The present invention has been disclosed and described herein in what is believed to be its most preferred embodiment. However, it is noted that variations will occur to those skilled in the art upon reading this disclosure and that such variations are believed to be encompassed by the present invention.

What is claimed is:

1. A process for purifying unreacted contaminated acrylonitrile, comprising the steps of:
   reacting, in a reaction vessel, a reactant with an excess of acrylonitrile;
   recovering unreacted acrylonitrile, in a contaminated form, from the vessel;
   treating the unreacted contaminated acrylonitrile with a base and removing salts formed to provide a treated acrylonitrile;
   heating the treated acrylonitrile in a heat exchanger under vacuum to a temperature above the melting point of the treated acrylonitrile but below about 172° F. to provide a heated fluid material;
   placing the fluid material in a distillation tower and distilling the fluid material under vacuum; and
   removing from the tower, acrylonitrile which has a boiling point below that of the treated acrylonitrile.

2. A process for purifying unreacted contaminated acrylonitrile, comprising the steps of:
   reacting a reactant with an excess of acrylonitrile;
   recovering unreacted contaminated acrylonitrile;
   treating the unreacted contaminated acrylonitrile with the lime in the presence of a catalytic amount of water and removing neural calcium salts formed to provide a treated acrylonitrile;
   heating the treated acrylonitrile in a heat exchanger to a temperature above the melting point of the treated acrylonitrile but below about 172° F. to provide a heated fluid material;
   placing the fluid material in a distillation tower and distilling the fluid material at a temperature above the melting point of the treated acrylonitrile but below about 172° F.; and
   removing from the tower, acrylonitrile which has a boiling point below that of the treated acrylonitrile.

3. A process for purifying unreacted contaminated acrylonitrile, comprising the steps of:
   synthesizing 2-acrylamido-2-methyl propane sulfonic acid by reacting sulfuric acid and isobutene with an excess of acrylonitrile;
   treating the unreacted contaminated acrylonitrile with a base and removing salts formed to provide a treated acrylonitrile;
   heating the treated acrylonitrile in a heat exchanger under vacuum to a temperature above the melting point of the treated acrylonitrile and below about 172° F. to provide a heated fluid material;
   placing the fluid material in a distillation tower and distilling the fluid material under vacuum; and
   removing from the tower, acrylonitrile which has a boiling point below that of the treated acrylonitrile.

4. A process for purifying unreacted contaminated acrylonitrile, comprising the steps of:
   synthesizing 2-acrylamido-2-methyl propane sulfonic acid by reacting sulfuric acid and isobutene with an excess of acrylonitrile;
   recovering unreacted contaminated acrylonitrile;
   treating the unreacted contaminated acrylonitrile with a base and removing salts formed to provide a treated acrylonitrile;
   heating the treated acrylonitrile in a heat exchanger under vacuum to a temperature in the range of about 110° F. to about 140° F. to provide a heated fluid material;
   placing the fluid material in a distillation tower and distilling the fluid material under vacuum, the fluid material entering the tower at a point in the lower half thereof, the distillation tower comprising a plurality of distillation trays, an opening in an upper half of the tower from which purified acrylonitrile is withdrawn and an opening in the lower half of the tower from which the fluid material is withdrawn; and
   removing from the opening in the lower half of the tower, a liquid having a boiling point above that of the treated acrylonitrile and returning at least a major portion of the removed fluid material to the heat exchanger, while withdrawing purified acrylonitrile from the opening in the upper half of the tower, the purified acrylonitrile having a boiling point below that of the treated acrylonitrile.

5. The process as claimed in claim 4, further comprising the steps of:
   placing a minor portion of the removed fluid material in a thin film evaporator, the minor portion the removed fluid material entering the evaporator at a point in the lower half thereof, the evaporator being maintained under vacuum at a temperature in the range of about 120° F. to about 145° F.;
   removing high boiling point contaminated fluid material from an opening in the lower half of the evaporator;
   removing low boiling point partially purified fluid material from an opening in the upper half of the evaporator and returning partially purified fluid material to an area of the tower above where fluid material enters the tower from the heat exchanger; and
   continuing distillation in the tower while removing and recovering purified acrylonitrile from the tower.

6. The process as claimed in any one of claims 1, 3, 4 or 5 wherein the base is lime in the presence of a catalytic amount of water and the salts removed are calcium salts.

7. The process as claimed in any one of claims 1, 3, 4 or 5 wherein the base is ammonia and the salts removed are ammonia salts.

8. The process as claimed in claim 7 wherein the ammonium slats are removed by centrifugation.

9. The process as claimed in claim 7 wherein the ammonium salts are removed by filtration.

10. The process as claimed in claim 7, wherein the ammonium salts are removed by settling.

11. The process as claimed in any one of claims 1, 2, 3, 4, or 5 wherein the salts are removed by a mechanical means selected from the group consisting of centrifugation, filtration and settling.

12. The process as claimed in claim 4 wherein the base is lime in water and the lime is present in an amount of about 0.5 to about 1.5 equivalents of lime per acid equivalent in the contaminated acrylonitrile.

13. The process as claimed in claim 12 wherein the water is present in an amount of about 1.0 to about 2.5% by weight based on the weight of the acrylonitrile.

14. The process as claimed in claim 13 wherein the lime is present in an amount of about 1.1 equivalents per equivalent of acid and the water is present in an amount of about 1.5% to about 2.0% by weight based on the weight of acrylonitrile.

* * * * *